United States Patent [19]

Svenson et al.

[11] Patent Number: 5,085,646

[45] Date of Patent: Feb. 4, 1992

[54] IMPLANT PASSAGEWAY

[76] Inventors: Jan A. Svenson, Solhemsgatan 16, Huskvarna S-561 35; Robert Axelsson, Box 4010, Huskvarna S-561 04, both of Sweden

[21] Appl. No.: 613,549
[22] PCT Filed: May 2, 1988
[86] PCT No.: PCT/SE88/00222
§ 371 Date: Nov. 27, 1990
§ 102(e) Date: Nov. 27, 1990
[87] PCT Pub. No.: WO89/10727
PCT Pub. Date: Nov. 16, 1989
[51] Int. Cl.$^5$ ................................. A61M 5/32
[52] U.S. Cl. ........................... 604/175; 604/8; 623/12
[58] Field of Search ............ 604/174, 175, 8, 9, 604/10, 29, 905; 523/1, 12

[56] References Cited

U.S. PATENT DOCUMENTS

| | | | |
|---|---|---|---|
| 3,298,372 | 1/1967 | Feinberg | 604/8 |
| 4,183,357 | 1/1980 | Bentley et al. | 604/175 |
| 4,623,348 | 11/1986 | Fent | 623/12 |
| 4,629,451 | 12/1986 | Winters et al. | 604/175 |
| 4,668,222 | 5/1987 | Poirier | 604/175 |
| 4,672,979 | 6/1987 | Pohndorf | 604/175 |
| 4,676,782 | 6/1987 | Yamamoto et al. | 604/175 |
| 4,701,180 | 10/1987 | Kelly et al. | 604/175 |
| 4,752,294 | 6/1988 | Lundgren . | |
| 4,781,176 | 11/1988 | Ravo | 623/12 |
| 4,854,316 | 8/1989 | Davis | 604/175 |

FOREIGN PATENT DOCUMENTS

| | | |
|---|---|---|
| 2645990 | 4/1977 | Fed. Rep. of Germany . |
| 2948949 | 3/1981 | Fed. Rep. of Germany . |
| 2143740 | 2/1985 | United Kingdom . |
| WO87/06122 | 10/1987 | PCT Int'l Appl. . |

Primary Examiner—John J. Wilson
Assistant Examiner—Frank A. LaViola
Attorney, Agent, or Firm—Merchant & Gould Smith, Edell, Welter & Schmidt

[57] ABSTRACT

Implant passageway for connection of body cavities, vessels or other organs to a device, container, pump or the like externally of the body, forming a tunnel and/or canal network inwardly of a smooth end portion for fixation and integration of the implant in the surrounding tissue.

2 Claims, 1 Drawing Sheet

IMPLANT PASSAGEWAY

TECHNICAL FIELD

The invention relates to an element for controlled growth of tissue into surgically intervened regions, e.g. for implant passageways, such an element being used to fix a prosthesis in the body or forming such a prosthetis itself.

BACKGROUND OF THE INVENTION

When an element is to be incorporated into a tissue or is to be implanted in such a way that it must pass through several tissues, i.e. in case of through the skin or through a mucous membrane, it is required that the element should be biocompatible, i.e. it must be accepted by the tissue, and the problem arises how to achieve a reliable retention of the element in the surrounding tissue to avoid a purely mechanical dislocation of the element. Unsatisfactory biocompatibility as well as insufficient retention leads to tissue irritation, possibly followed by tissue rupture at the element. This means formation of reactive zones of connective tissue with a more or less pronounced streak of inflammation leading to the element no longer being harmoniously incorporated in the tissue region; the element starts to wander and loses its function. Furthermore, tissue irritation at implant passageways leads to downgrowth of epithelium around the element and, as a consequence thereof, finally to rejection.

In order to solve these problems, the element according to the invention has obtained the characteristics of the claims.

BRIEF DESCRIPTION OF THE DRAWINGS

For explanation of the invention in more detail reference is made to the accompanying drawings, wherein.

DETAILED DESCRIPTION

Figure 1:
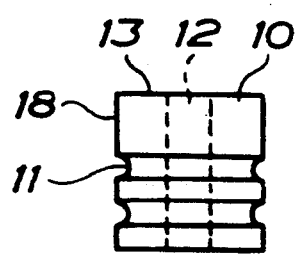
FIG. 1 shows a cylindrical implant element having peripheral grooves and a central passage.
Figure 2:
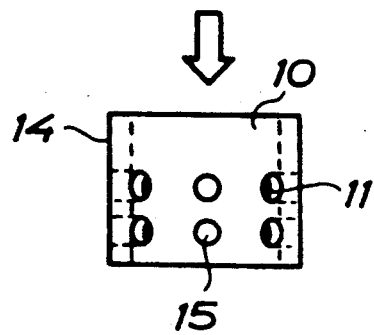
FIG. 2 illustrates an outer socket having through holes of the same levels as the grooves of the cylinder of FIG. 1.
Figure 3:
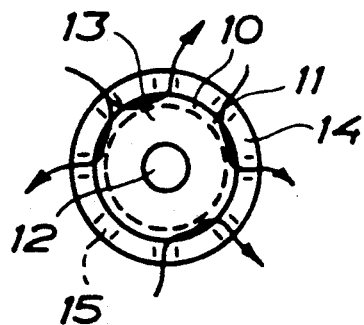
FIG. 3 shows the cylinder and tee socket pressed together to form a unit providing a tunnel and/or canal network within the periphery of the implant element.

In the illustrated embodiment, the element 10 is tubular and can comprise e.g. an implanted conduit for peritoneal dialysis (abdominal dialysis). The conduit can be rigid or flexible. It forms a number of tunnel and/or canal networks 11, which are separated from the passage 12 through the element by a solid wall 13 and from the exterior surface of the element by an ingrowth zone 14, the openings of which are indicated at 15 and form circular apertures. The connective tissue, which is indicated at 16, grows into the tunnel and/or canal network 11, matures and attains a structural organization resulting in the epithelium 17 being prevented from growing down along the surface of the element and infiltrating the layer of connective tissue next to the element to enclose eventually the element 10, which leads to rejection of the element. The tissue ingrowth into the tunnel and/or canal network 11 should be such that the connective tissue inside the tunnel and/or canal network 11 becomes complete and attains full maturity, i.e. the tunnel and/or canal network 11 should be sufficiently large to allow the connective tissue cells as well as the blood-vessels necessary for the maintenance of the connective tissue to grow thereinto, thus creating conditions for the generation of connective tissue fibres and matrix by the connective tissue cells and for the maturation of the components of the connective tissue and normal renewal thereof, requiring that no part of the tunnel and/or canal network 11 should have a diameter less than 30 μm.

According to the invention, the surfaces of the element 10, which are exposed to the surrounding tissue, consist of a biocompatible material, titanium being an excellent material of this kind. The element 10 as a whole can consist of titanium, but preferably the element 10 is coated on said surfaces, i.e. the exterior surface of the element inside the tunnel and/or canal network il, with titanium by a thin layer thereof being deposited on a substrate by vacuum evaporation. This substrate can be rigid or flexible and can consist of e.g. silicone rubber, polyester or polytetrafluoro ethylene. In the illustrated embodiment, the openings 15 of the tunnel and/or canal network have sharp edges, but the edges can be formed in another way, e.g. as beveled edges on the outside of the element or inside the tunnel and/or canal network 11, or they can be rounded.

When an implant passageway is implanted in the body tissue in the way which has been described, the connective tissue has the opportunity to mature adjacent to the surface of the element 10 and inside the tunnel and/or canal network 11 in order to achieve a reliable and permanent retention of the element by preventing the epithelium from growing down around the element at the implant passageway.

Figure 4:
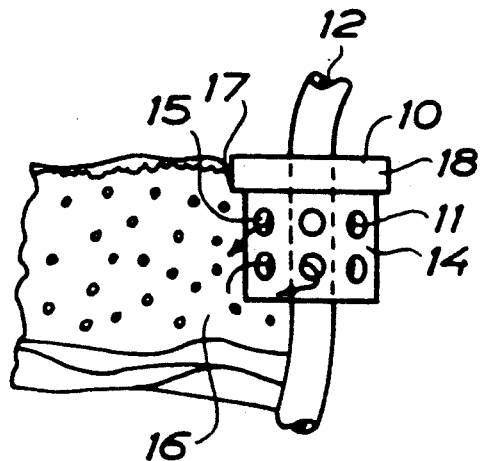
FIG. 4 is an illustration similar to FIG. 3 but with a diametrically wider flange on the upper end portion of the cylinder.

The portion of the surface of the element 10, located immediately above the uppermost tunnel and/or canal opening 11 provided in the wall of the element, which is exposed to the epithelium layer 17, therefore should be suitably profiled. e.g. widened as in FIG. 4. This arrangement further prevents downgrowth of epithelium along the surface of the element during the time required for the granulation tissue of the wound region to mature into a firm, structured connective tissue.

The tunnel and/or canal network 11 can be constructed in several different ways, e.g. as a labyrinth system.

What is claimed is:

1. Implant passageway for connection of body cavities, vessels and other organs to a device externally of the body, having a biocompatible surface and comprising a tubular element forming a through passage and peripheral grooves on the outside of the curved surface thereof inwardly of an end portion having a smooth surface, and a socket surrounding the tubular element and forming through holes in register with said grooves and together with the tubular element defining a number of passage networks with a minimum cross-sectional dimension of 30 μm for controlled growth of surrounding tissue thereinto in order to prevent epithelium from growing down around the passageway and achieve a reliable and permanent retention thereof.

2. Implant passageway as in claim 1 wherein said end portion of the element is widened in relation to the remaining portion of the element.

* * * * *